US009228121B2

(12) United States Patent
de Oliveira Filho et al.

(10) Patent No.: US 9,228,121 B2
(45) Date of Patent: Jan. 5, 2016

(54) PROCESS FOR THE CO-ENCAPSULATION OF BIOCIDALLY ACTIVE COMPOUNDS IN CLAY MINERALS FUNCTIONALIZED BY NITROGEN COMPOUNDS

(75) Inventors: Antonio Pedro de Oliveira Filho, Sao Paulo (BR); Wagner Claudio Da Silva, Sao Paulo (BR); Manlio Gallotti, Sao Paulo (BR); Alexandra Paschoalin Menezes, Sao Paulo (BR); Karine Framesqui Righi, Sao Paulo (BR); Marcia Regina Da Silva Rios, Sao Paulo (BR)

(73) Assignee: Clariant S.A., Sao Paulo (BR)

( * ) Notice: Subject to any disclaimer, the term of this patent is extended or adjusted under 35 U.S.C. 154(b) by 171 days.

(21) Appl. No.: 13/580,546

(22) PCT Filed: Feb. 15, 2011

(86) PCT No.: PCT/EP2011/000683
§ 371 (c)(1),
(2), (4) Date: Aug. 22, 2012

(87) PCT Pub. No.: WO2011/103969
PCT Pub. Date: Sep. 1, 2011

(65) Prior Publication Data
US 2012/0316259 A1 Dec. 13, 2012

(30) Foreign Application Priority Data

Feb. 23, 2010 (EP) .................................. 10001837
Dec. 24, 2010 (EP) .................................. 10016075

(51) Int. Cl.
| | |
|---|---|
| C09D 5/14 | (2006.01) |
| C09D 133/08 | (2006.01) |
| A01N 25/28 | (2006.01) |
| A01N 33/12 | (2006.01) |
| A01N 43/80 | (2006.01) |
| A01N 47/12 | (2006.01) |
| A01N 55/06 | (2006.01) |
| A01N 55/08 | (2006.01) |
| A01N 57/20 | (2006.01) |
| A01N 59/16 | (2006.01) |
| A01N 59/20 | (2006.01) |
| A01P 1/00 | (2006.01) |
| C09K 8/03 | (2006.01) |
| A01N 33/04 | (2006.01) |
| A01N 33/08 | (2006.01) |
| A01N 57/34 | (2006.01) |
| C09D 7/12 | (2006.01) |
| C08K 3/34 | (2006.01) |
| C08K 9/04 | (2006.01) |

(52) U.S. Cl.
CPC . *C09K 8/03* (2013.01); *A01N 33/04* (2013.01);
*A01N 33/08* (2013.01); *A01N 33/12* (2013.01);
*A01N 43/80* (2013.01); *A01N 47/12* (2013.01);
*A01N 57/34* (2013.01); *C09D 5/14* (2013.01);
*C09D 7/1225* (2013.01); *C08K 3/346*
(2013.01); *C08K 9/04* (2013.01)

(58) Field of Classification Search
CPC ............ C09K 8/03; C09K 3/346; C09K 9/04;
A01N 33/04; A01N 33/08; A01N 33/12;
A01N 43/80; A01N 47/12; A01N 57/34;
C09D 5/14; C09D 7/1225
USPC ............................................ 524/83, 236, 403
See application file for complete search history.

(56) References Cited

U.S. PATENT DOCUMENTS

| | | | |
|---|---|---|---|
| 2,531,427 A | 11/1950 | Hauser | |
| 3,467,208 A | 9/1969 | Kelly | |
| 3,831,678 A | 8/1974 | Mondshine | |
| 4,552,591 A * | 11/1985 | Millar ........................ | 106/18.33 |
| 4,556,426 A | 12/1985 | Chesney et al. | |
| 4,752,342 A | 6/1988 | Tatum et al. | |
| 4,849,006 A | 7/1989 | Knudson | |
| 5,164,096 A | 11/1992 | Nunn | |
| 5,219,875 A | 6/1993 | Sherba et al. | |
| 5,416,109 A | 5/1995 | Donofrio et al. | |
| 5,421,867 A | 6/1995 | Yeager et al. | |
| 6,133,300 A | 10/2000 | Smith et al. | |
| 6,165,485 A | 12/2000 | Alther | |

(Continued)

FOREIGN PATENT DOCUMENTS

| | | |
|---|---|---|
| CA | 2175480 | 5/1995 |
| CN | 1450015 | 10/2003 |

(Continued)

OTHER PUBLICATIONS

International Search Report for PCT/EP2011/000683, dated Sep. 5, 2011.
International Preliminary Report on Patentability for PCT/EP2011/000683, dated Jun. 1, 2012.
International Search Report for PCT/BR2013/000340, dated Mar. 21, 2014.
English Abstract for CA 2175480, dated May 11, 1995.
English Abstract for JP H08193013, dated Jul. 30, 1996.
English Abstract for JP 2003342527, dated Dec. 3, 2003.
English Abstract for JP H08217519, dated Aug. 27, 1996.
English Abstract for WO 93/02668, dated Feb. 18, 1993.

*Primary Examiner* — Kriellion Sanders
(74) *Attorney, Agent, or Firm* — Tod A. Waldrop

(57) ABSTRACT

This invention relates to a process for the co-encapsulation of biocidally active ingredients in a clay mineral, the process comprising the step of bringing the clay mineral into contact with a biocidally active nitrogen compound that contains at least one hydrocarbon group with 6 to 20 carbon atoms, and at the same time or subsequently with at least one biocidally active compound selected from the group consisting of 2-n-octyl-4-isothiazoline-3-one, 3-iodopropenylbutyl-carbamate and tetrahis(hydroxymethyl)phosphonium sulfate. And the use of such encapsulated product in water based paints, coatings and varnishes.

12 Claims, No Drawings

(56) References Cited

U.S. PATENT DOCUMENTS

| | | |
|---|---|---|
| 6,521,678 B1 | 2/2003 | Chaiko |
| 7,429,392 B2 | 9/2008 | Baum et al. |
| 2005/0126430 A1 | 6/2005 | Lightner et al. |
| 2008/0206295 A1 | 8/2008 | Bernardini et al. |
| 2008/0281017 A1 | 11/2008 | Weitzel et al. |
| 2011/0009268 A1* | 1/2011 | Uhr et al. ............ 504/143 |
| 2011/0077278 A1 | 3/2011 | Smith et al. |
| 2011/0097371 A1* | 4/2011 | Premachandran et al. ... 424/409 |

FOREIGN PATENT DOCUMENTS

| | | |
|---|---|---|
| EP | 0215562 | 3/1987 |
| GB | 1488891 | 10/1977 |
| JP | H08193013 | 7/1996 |
| JP | H08217519 | 8/1996 |
| JP | 2003342527 | 12/2003 |
| WO | WO 93/02668 | 2/1993 |
| WO | WO 95/12315 | 5/1995 |
| WO | WO 97/31709 | 9/1997 |
| WO | WO 98/08380 | 3/1998 |

* cited by examiner

PROCESS FOR THE CO-ENCAPSULATION OF BIOCIDALLY ACTIVE COMPOUNDS IN CLAY MINERALS FUNCTIONALIZED BY NITROGEN COMPOUNDS

FIELD OF THE INVENTION

This invention relates to a process for the co-encapsulation of biocidally active compounds in clay minerals which are functionalized by hydrocarbon-substituted nitrogen compounds. A preferred embodiment of this invention is the use of hydrocarbon-substituted nitrogen compounds as vehicle to carry on the active ingredient inside the layers of the clay mineral. The process makes it possible to encapsulate a large quantity and a variety of active ingredients inside layers of a clay mineral.

BACKGROUND OF THE INVENTION

The process of production of clay minerals having a lipophilic characteristic ("organoclays") using ammonium quaternary salts to give to clay minerals said lipophilic characteristic is known. Clay minerals, especially smectite, are a class of minerals that contain in their structural formula dioctahedral aluminous species which can be represented by the formula $$[(Al_{(2-y)}Mg_y)(Si_{(4-x)}Al_x)O_{10}(OH)_2][M_{(x+y)}]nH_2O$$

wherein:

x is the amount of aluminum atoms exchangeable from octahedral sheet, and y is the amount of silicon atoms exchangeable from tetrahedral sheet, and $M_{(x+y)}$ are monovalent cations present in the clay structure to compensate the resultant charge after the exchange of aluminum and silicon have occurred into the octahedral and tetrahedral sheets, respectively.

Regarding the total amount of cation exchangeable capacity, (x+y) comprises the range $0.2 \leq (x+y) \leq 0.6$. This range represents the minimum and maximum milliequivalents of cation exchangeable in 100 g of clay mineral.

U.S. Pat. No. 2,531,427 discloses that if $M_{(x+y)}$ is exchanged by an ammonium quaternary salt two different effects are observed in the clay mineral. The replacement of the cation by the ammonium quaternary salt causes an enlargement of the distance between layers of the clay mineral, and the clay mineral surface becomes hydrophobic because of the presence of the alkyl groups introduced by the ammonium quaternary salt. The objective of that invention was to provide a modification of the clay mineral by replacing the interlayer cation by amines in order to give to the clay mineral surface a substantial gelling characteristic which swelled when dispersed in an organic liquid.

Further state of the art is summarized as follows.

U.S. Pat. No. 3,467,208 discloses the application of bentonite treated by long-chain amines in order to give good thixotropy for an oil based drilling mud and to avoid the fluid loss during the well drilling process.

U.S. Pat. No. 3,831,678 discloses the use of a clay which has been organically functionalized by dimethyltallow hydrogenated ammonium salts as viscosifier in oil based drilling fluids.

U.S. Pat. No. 4,752,342 teaches a process for the replacement of sodium by an ammonium quaternary salt in a clay mineral.

The state of the art presented above does not present any disclosure about encapsulation or co-encapsulation of biocidally active ingredients interlayer of the clay minerals. It discloses the preparation of organophilic clays with several types of amines and ammonium quaternary salts.

U.S. Pat. No. 5,164,096 discloses the use of biocide contained within the core of the microcapsules made of a gum gelatin membrane. These microcapsules are used to treat a water system by controlled release of the biocide actives.

WO-A-93/02668 discloses the microencapsulation of at least one active ingredient, contained in an hydrophilic internal core, coated by a coat of copolymer of ethylene and vinyl acetate (EVA) or a copolymer of vinylidene chloride and vinyl chloride and other types of polymers.

U.S. Pat. No. 6,165,485 discloses that a bentonite based organoclay, when mixed with a biocidal quaternary amine containing a benzyl molecule within its structure, acts as a reasonably effective biocide.

U.S. Pat. No. 6,521,678 describes a method for preparing organoclays with a substantially monomolecular layer of water soluble polymer to the clay; applying a surfactant to the clay to modify the hydrophilic/hydrophobic balance of surfaces of the clay and separate out the organoclay from the water.

U.S. Pat. No. 7,429,392 discloses the use of biocides bonded to solid resins particles in order to confer antimicrobial protection to highly alkaline coating films, e.g. paints, leading to higher stability in the pH of the paint and delayed release of the biocide.

It has been observed that there are biocidally active ingredients that cannot be encapsulated into organophilic clay using the encapsulation modifiers of the state of the art. The problem of the instant invention was to find an encapsulation modifier that allows such biocidally active ingredients to be encapsulated in a clay mineral.

It has been found that the use of clay mineral functionalized by hydrocarbon-substituted nitrogen compounds allows co-encapsulation of several types of biocidally active ingredients which otherwise can not be inserted into the interlayer of the clay mineral without the presence of the hydrocarbon-substituted nitrogen compounds.

DETAILED DESCRIPTION OF THE INVENTION

The instant invention relates to a process for the co-encapsulation of biocidally active ingredients in a clay mineral, the process comprising the step of bringing the clay mineral into contact with a biocidally active nitrogen compound that contains at least one hydrocarbon group with 6 to 20 carbon atoms, and at the same time or subsequently with at least one biocidally active compound selected from the group consisting of 2-n-octyl-4-isothiazoline-3-one, 3-iodopropenylbutylcarbamate and tetrakis(hydroxymethyl)phosphonium sulfate.

Another object of the invention is a biocidally active clay mineral, obtainable by bringing the clay mineral into contact with a nitrogen compound that contains at least one hydrocarbon group with 6 to 20 carbon atoms, and at the same time or subsequently with at least one biocidally active compound selected from the group consisting of 2-n-octyl-4-isothiazoline-3-one (OIT), 3-iodopropenylbutylcarbamate (IPBC) and tetrakis(hydroxymethyl)phosphoniumsulfate (THPS).

Another object of the invention is the use of a biocidally active nitrogen compound having at least one hydrocarbon group with 6 to 20 carbon atoms to encapsulate a biocidal composition, said composition comprising at least one of OIT, IPBC and THPS, in a clay mineral.

The expressions "actives" or "active ingredients" as used herein refer to biocidally active compounds. The expression "biocidally active" means that the respective compound is capable of killing microorganisms or preventing the growth of microorganisms (bacteriostatic) which can spoil or contaminate a raw material or product. Microorganisms are for example bacteria, fungi and algae.

Preferably, the clay minerals comprise smectite group mineral in a concentration ranging between 60-95 wt.-%. Additionally, minerals like quartz, cristobalite, feldspar, pirite, carbonates, chlorite, caolinite, mica and illite may be present. The preferred mineral species from the smectite group mineral are beidellite, hectorite, montmorillonite, nontronite, sauconite, saponite and volconscoite. The structural formula of smectites of the dioctahedral aluminous species may be represented by $$[(Al_{(2-y)}Mg_y)(Si_{(4-x)}Al_x)O_{10}(OH)_2][M_{(x+y)}]nH_2O$$

wherein:
x is the amount of aluminum atoms exchangeable from octahedral sheet, and
y is the amount of silicon atoms exchangeable from tetrahedral sheet, and
$M_{(x+y)}$ are monovalent cations present in the clay structure to compensate the resultant charge after the exchange of aluminum and silicon have occurred into the octahedral and tetrahedral sheets, respectively.

Regarding the total amount of cation exchangeable capacity, (x+y) comprises the range $0.2 \leq (x+y) \leq 0.6$. This range represents the minimum and maximum milliequivalents of cation exchangeable in 100 g of clay mineral. n is the molar amount of water present in the clay mineral, which can take values from 0 to 7, preferably 2 to 6.

Usually, clay minerals from the smectite group are also known as bentonites.

The biocidally active nitrogen compound may be chosen from a variety of generic groups. Common to all of the following formulae and the definition of the residues is the requirement that at least one of the residues is a hydrocarbyl residue having at least 6 and at most 20 carbon atoms.

In one preferred embodiment, the nitrogen compound is a quaternary ammonium compound. Preferred quaternary ammonium compounds correspond to the formula $$[R^1R^2R^3R^4N]^+X^- \quad (1)$$

wherein $R^1$, $R^2$, $R^3$, and $R^4$ independently are linear, branched, cyclic, saturated or unsaturated hydrocarbon groups, and X is an anion. $R^1$, $R^2$, $R^3$ and $R^4$ may contain between 1 and 30 carbon atoms, provided that at least one of $R^1$, $R^2$, $R^3$ and $R^4$ contains from 6 to 20 carbon atoms. The sum of the number of carbon atoms in $R^1$, $R^2$, $R^3$, and $R^4$ preferably ranges from 9 to 30. $R^1$, $R^2$, $R^3$, and $R^4$ may be alkyl, alkenyl, alkynyl, cycloalkyl or aryl groups. X may be chloride, carbonate, bicarbonate, nitrate, bromide, acetate or carboxylates.

A preferred quaternary ammonium compound corresponds to the formula $$[R^1(CH_3)_3N]^+X^- \quad (2)$$

wherein $R^1$ is a linear or branched $C_6$-$C_{20}$ saturated or unsaturated hydrocarbon group, such as an alkyl, alkenyl, or alkynyl group and X is defined as above. More preferably, $R^1$ is a linear $C_6$-$C_{18}$ saturated or unsaturated group and X is chloride, carbonate, or acetate.

Another preferred quaternary ammonium compound corresponds to the formula $$[R^1R^2(CH_3)_2N]^+X^- \quad (3)$$

wherein $R^1$ is a linear or branched $C_6$-$C_{20}$ saturated or unsaturated hydrocarbon group or $C_6$-$C_{20}$ substituted, benzyl or unsubstituted aryl group, $R^2$ is a linear or branched $C_1$-$C_{20}$ saturated or unsaturated group or $C_6$-$C_{20}$ substituted, benzyl or unsubstituted aryl group, and X is defined as above. Preferably, $R^1$ and $R^2$ independently are linear or branched $C_8$-$C_{16}$ saturated or unsaturated groups. In a more preferred embodiment, $R^1$ and $R^2$ independently are linear or branched $C_8$-$C_{12}$ saturated or unsaturated groups and X is chloride, carbonate, sulfate, or acetate.

The expression substituted as used herein means substitution with a $C_1$-$C_4$ alkyl group.

Another preferred quaternary ammonium compound corresponds to the formula $$[R^1R^2(CH_3)_2N]^+X^- \quad (4)$$

wherein $R^1$ is a substituted or unsubstituted benzyl group, $R^2$ is a linear $C_{10}$ to $C_{20}$ saturated or unsaturated hydrocarbon group, and X is defined as above. According to a preferred embodiment, $R^1$ is benzyl, $R^2$ is a linear $C_{12}$-$C_{18}$ saturated or unsaturated hydrocarbon group, and $X^-$ is chloride.

Another quaternary ammonium compound preferred for use in the present invention corresponds to the formula $$[R^1R^2N(CH_3)((CH_2CH_2O)_nH)]^+X^- \quad (5)$$

wherein $R^1$ is a $C_6$-$C_{20}$ linear or branched, substituted or unsubstituted alkyl group or a $C_6$-$C_{20}$ substituted or unsubstituted aryl group, $R^2$ is a $C_1$-$C_{20}$ linear or branched, substituted or unsubstituted alkyl group or a $C_6$-$C_{20}$ substituted or unsubstituted aryl group, n is an integer from 1 to 5, and X is defined as above. Preferably, $R^1$ and $R^2$ are linear or branched $C_8$-$C_{10}$ substituted or unsubstituted alkyl or aryl groups and more preferably are decyl. $X^-$ is preferably chloride.

Another preferred quaternary ammonium compound corresponds to the formula $$[R^1R^2R^3(CH_3)N]^+X^- \quad (6)$$

wherein $R^1$, $R^2$ and $R^3$ independently are linear or branched $C_6$-$C_{20}$ saturated or unsaturated groups. More preferably $R^1$, $R^2$ and $R^3$ independently are linear or branched $C_8$-$C_{10}$ saturated or unsaturated groups. X is preferably chloride.

One, two or more of quaternary ammonium compounds can be used to produce an organoclay system which is the vehicle to the active ingredients, i.e. into which the active ingredients are co-encapsulated.

In cases wherein $X^-$ means an ion with a charge of more than one, e.g. a carbonate or sulfate ion, its stoichiometric index is to be divided by the charge in order to achieve electric neutrality.

Apart from said ammonium compounds, nitrogen containing compounds comprising at least one hydrocarbon group with 6 to 20 carbon atoms that do not necessarily carry a charge may be used according to the instant invention. Examples of such nitrogen containing compounds are alkyl amines, amines, ether diamines and sternamines.

A preferred alkylamine has the formula $$[R^1R^2R^3N] \quad (7)$$

wherein $R^1$, $R^2$ and $R^3$ independently are hydrogen, linear or branched $C_6$-$C_{20}$ saturated or unsaturated hydrocarbon groups. More preferably $R^1$, $R^2$ and $R^3$ independently are linear or branched $C_8$-$C_{10}$ saturated or unsaturated groups. The saturated or unsaturated groups are more preferably alkyl groups, alkenyl groups or cycloalkyl groups having 6 to 20 carbon atoms.

A preferred etheramine corresponds to the generic formula

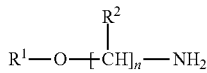 (8)

wherein
$R^1$ is $(C_2-C_{30})$-alkyl or $C_5$- to $C_{12}$-cycloalkyl;
$R^2$ is H, $CH_3$, $CH_2CH_3$ or $(CH_2)_2CH_3$,
n is 1, 2, 3, 4 or 5

Apart from the etheramines, their salts may be used. Suitable etheramine salts are represented by the generic formula

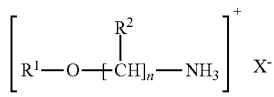 (9)

wherein
$R^1$ is $(C_2-C_{30})$-alkyl or $C_5$- to $C_{12}$-cycloalkyl;
$R^2$ is H, $CH_3$, $CH_2CH_3$ or $(CH_2)_2CH_3$,
n is 1, 2, 3, 4 or 5 and
X is an anion such that the etheramines compound is water soluble.

The use of ether amine salts according to formula 9 is preferred over the use of ether amines according to formula 8. Ether amine salts according to formula 9 show superior permeation ability into the layers of the clay mineral.

A preferred ether diamine corresponds to the generic formula

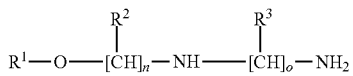 (10a)

Again, the salts of such ether diamines may be used in this invention. Preferred salts correspond to the formula

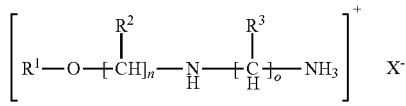 (10b)

wherein for both formula 10a and 10b
$R^1$ is $(C_2-C_{30})$-alkyl or $C_5$- to $C_{12}$-cycloalkyl;
$R^2$, $R^3$ are H, $CH_3$, $CH_2CH_3$ or $(CH_2)_2CH_3$,
n, o are 1, 2, 3, 4 or 5 and
X is an anion such that the etheramine compound is water soluble.

Sternamines and their salts also can be used as vehicle in order to co-encapsulate active substances or metal with bio cide activity. A suitable sternamine corresponds to the generic formula

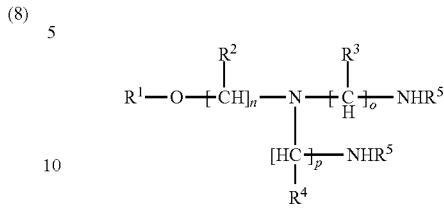 (11)

wherein
$R^1$ is $(C_2-C_{30})$-alkyl or $C_5$- to $C_{12}$-cycloalkyl;
$R^5$ corresponds to the formula

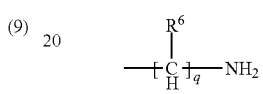 (12)

$R^2$, $R^3$, $R^4$, $R^6$ are H, $CH_3$, $CH_2CH_3$ or $(CH_2)_2CH_3$,
n, o, p, q are 1, 2, 3, 4 or 5.

Again, the salts obtainable from the compounds of formula 11 by protonation of the free $NH_2$ groups may also be used in this invention.

Common to all of formulae 8-12 is that $R^1$ is preferably an alkyl or cycloalkyl group having 6 to 20 carbon atoms, particularly 8 to 16 carbon atoms. The cycloalkyl group may be bicyclic, tricyclic or higher.

The biocidally active compound has to comprise at least one of OIT, IPBC and THPS. It may contain any binary combination of these compounds, e.g. OIT and IPBC, OIT and THPS, IPBC and THPS, OIT and THPS and the ternary combination of OIT, IPBC and THPS.

Preferably, in order to obtain multifunctional synergistic compositions, at least one other biocidally active compound which is different from a nitrogen compound that contains at least one hydrocarbon group with 6 to 20 carbon atoms, or 2-n-octyl-4-isothiazoline-3-one (OIT), 3-iodopropenylbutyl-carbamate (IPBC) and tetrakis(hydroxymethyl)phosphoniumsulfate (THPS) is present.

A suitable active ingredient is a substance that contains in its structure one or more functional groups which give to the molecule biocidally activity. Preferred generic classes of active ingredients are etheramines, amines, phenols and its derivates; aldehydes; formaldehyde releasing compounds; acetaldehyde releasing compounds; succinaldehyde releasing compounds; 2-propenaldehyde releasing compounds; acids; acid esters; amides; carbamates; dibenzamides; pyridine derivatives; azoles; N compounds; S heterocyclics; N-Haloalkylthio compounds; compounds containing activated halogen atom; surface activation agents; organometallic compounds; and oxidizing agents.

Examples of these active ingredients are: Ethanol, 1-Propanol, 2-Propanol, 1,2-Propanediol, 2-Phenoxyethanol, 1-Phenoxypropanol, Formaldehyde, Glutaraldehyde, Acetaldehyde, Glyoxal, Ethylene Glycol hemiformal, Ethylene Glycol bishemiformal, 1,3-dioxolane, 3,3'-Methylenebis(5-methyl-1,3-oxazolidine), Hexahydro-1,3,5-tris(2-hydroxyethyl)-s-triazine, Hexahydro-1,3,5-tris(2-hydroxypropyl)-s-triazine, Bis(tetrakis(hydroxymethyl)phosphonium)sulfate, 1,3-Bis(hydroxymethyl)5,5-dimethyl-2,4-dioxoimidazolidine), 6-Acetoxy-2,4-dimethyl-1,3-dioxane, 2,5-Dimethoxytetrahydrofuran, Phenol, Chloromethylphenol, 4-Chlorophenol, Formic acid, Acetic acid, sorbic acid, benzoic acid, boric acid, Ethyl formate, Benzyl bromoacetate, dimethyl dicarbonate, N'-(3,4-dichlorophenyl)-N,N-dimethylurea, N'-(4-chlorophenyl)-N'-(3,4-dichlorophenyl)urea), 3-Iodopropynylphenylcarbamate, 3-Iodopropynylcarbamate, Methyl-N-(2-benzimidazolyl)carbamate, 4,4'-Diamidinophenoxypropane, 4,4'-Diamidino-2,2'-dibromodiphenoxypropane, Pyridine-N-oxides, 8-Quinolinol, 1-[2-(2,4-Dichlorophenyl)-4-propyl-1,3-dioxolan-2yl-methyl]1H-1,2,4-triazole, 2-methyl-4-isothiazolin-3-one, 5-Chloro-2-methyl-4-isothiazolin-3-one, 4,5-dichloro-2-(n-octyl)-4-isothiazolin-3-one, 1,2-benzisothiazolin-3-one, N-butyl-1,2-benzisothiazolin-3-one), N,N,dimethyl-N'-tolyl-N'-dichlorofluoromythylthiosulphamide, 2-Bromoacetamide, 2,2-Dibromo-3-nitrilopropionamide, 2-bromo-2-nitro-propan-1-ol, 2-bromo-2-nitropro-pane-1,3-diol, poly(hexamethylenebiguanide) hydrochloride, sodium ethylmercury thiosalicylate, trichloromelamine and 1,3-dichloro-5,5-dimethylhydantoin.

Metallic ions which have a biocidal property may also be employed as further components. They are preferably employed for surface modification of the clay mineral. The following metallic ions are preferred: silver, copper, zinc, molybdenum and titanium.

The combined amount of all biocides, i.e. nitrogen compound that contains at least one hydrocarbon group with 6 to 20 carbon atoms and OIT, IPBC or THPS or their mixture, and, if present metal ions, and, if present one or more any other biocidally active compound which is different from a nitrogen compound that contains at least one hydrocarbon group with 6 to 20 carbon atoms, or 2-n-octyl-4-isothiazoline-3-one (OIT), 3-iodopropenylbutylcarbamate (IPBC) and tetrakis(hydroxymethyl)phosphoniumsulfate (THPS) in the finished biocidally active clay mineral is preferably from 1 to 60, particularly from 5 to 55, more preferably from 10 to 45 wt.-%, relative to the weight of the finished biocidally active clay mineral.

The weight ratio between OIT, IPBC or THPS or their mixture and the nitrogen compound that contains at least one hydrocarbon group with 6 to 20 carbon atoms is preferably in the range of 1:10 to 10:1, particularly 1:5 to 5:1, more preferably 1:2 to 2:1 by weight.

In the embodiment wherein the finished biocidally active clay mineral contains metal ions, one or more any other biocidally active compound, or both, the total amount of the metal ions, if present, is preferably between 0.5 and 21 wt.-%, particularly between 8 and 13 wt.-%, the wt.-% being relative to the combined amount of all biocides, including the metal ions.

In the embodiment wherein the finished biocidally active clay mineral contains metal ions, one or more any other biocidally active compound, or both, the total amount of one or more any other biocidally active compound which is different from a nitrogen compound that contains at least one hydrocarbon group with 6 to 20 carbon atoms, or 2-n-octyl-4-isothiazoline-3-one (OIT), 3-iodopropenylbutylcarbamate (IPBC) and tetrakis(hydroxymethyl)phosphoniumsulfate (THPS) is preferably between 0.5 and 21 wt.-%, particularly between 8 and 13 wt.-%, the wt.-% being relative to the combined amount of all biocides, including the other biocidally active compound.

Compounds according to the instant invention are useful for application in agriculture, oil industry, as biocide to varnishes, paints, coatings, mortars, grouts and in corrosion inhibitor compositions.

The compounds according to the instant invention when used in paints, varnishes and coating materials are capable of showing their biocidal activity even in case of exposition of the paints, varnishes and coating materials to a damp environment or water.

The consequence of microbiological infestation by fungus and algae is normally the presence of spots on the surface. As well as disfiguring the surface, the organisms can actually penetrate the paints, varnishes and coating materials and make them more permeable to water. Growth can also develop under the paints, varnishes and coating materials and cause loss of adhesion.

Commonly, fungus and algae growth are favored by bacterial infestation, which can lead to a pH decrease due to the excretion of acid compounds by said microorganisms. Differently from typical fungi and algae infestation, bacterial growth is not perceived visually, then being an important factor for general microbiological infestation.

It has been known that besides the use of bactericidal agents required for in can preservation of paints, varnishes and coatings, fungicidal and/or algicidal as well as bactericides are also added in order to preserve the films formed by paints, varnishes and coatings. Generally, the use of biocidally active agents is recommended for all kinds of paints, coatings and varnishes, but they are of paramount importance for critical environments.

The main problem related to the use of biocides in paints, coatings and varnishes is leaching. Water soluble biocides may leach to the environment when exposed to a damp environment or water, what, depending on the weathering situation, leads to poor effectiveness in short periods of time and infestation of films by microorganisms, therefore requiring a new surface treatment.

Besides the leaching problem, the high toxicity of many commercially available biocidally active agents is of great concern for producers of paints, varnishes and coatings, thus safer biocidally active agents of low toxicity to the environment and to the human beings are required.

Common biocidally active agents such as heterocyclic compounds, carbamates, halogenated compounds, amides and trazines, shows among other problems, a tendency to change their colour to yellow and to degrade under high temperatures and the influence of light, these effects limiting their use.

The state of the art in paints, coatings and varnishes preservation is the association of different biocidally active agents and the use of encapsulated biocidally active agents in polymeric material carriers, for control of microbiological growth. The encapsulation technology has been used for different applications in order to deliver toxicological, stability and time-effectiveness benefits.

The controlled release of biocidally active agents is important when there is immediate consumption of the biocidally active agent upon its application, reducing the need of a new application, and adding a preservative characteristic to the biocidally active agent. When a product requires bacteriostatic action, the controlled release increases that product's shelf life.

One embodiment of the present invention relates to the use of the compounds according to the instant invention in paints, varnishes and coatings, including marine applications. The use of the compounds according to the instant invention in such applications is effective in preventing microbial growth even in damp environments.

Some properties of the compounds according to the instant invention include, but are not limited to: higher UV radiation stability; higher thermal stability; controlled release of biocides; high biocide effectiveness as function of time; reduced toxicity and higher environmental compatibility.

In contrast to the prior art, the use of clay minerals as carriers is significantly less expensive than the use of polymeric resins. Moreover, the nitrogen compounds used for functionalization of the clay mineral which are also effective as algicide and not commonly used in paints, coatings and varnishes, are significantly less toxic than typically used algicidal molecules, such as N,N-t-butyl-N,N,N-ethyl-6-methylthio-1,3,5-triazine-2,4-diyldiamine (terbutryn) and 3-(3, 4-dichlorophenyl)-1,1-dimethylurea (diuron).

The preferred total amount of the encapsulated biocide in the paint, coating or varnish varies from 0.01% to 10% by weight of the treated paint, coating or varnish.

The biocide encapsulating process includes an inorganic material as encapsulating agent and biocide components. A paint, coating or varnish containing the encapsulated biocide has antimicrobial properties and low biocide leaching compared to non-encapsulated biocide treated paint, coating or varnish.

The encapsulating clay mineral particles work as biocide molecules inert carriers. The encapsulating process aims at improving interaction properties, i.e. polar and hydrophilic biocides absorption by plasmatic membrane adding hydrophobic characteristics to the biocide compound.

Another particularity of the use of such encapsulated biocides may be a slight modification of rheological properties of water based paints, coatings and varnishes, related to the presence of clay minerals.

Other embodiments of the present invention are water based paints, coatings and varnishes which comprises the encapsulated biocide and a binder.

Paints are coatings which contain solid pigments dispersed in a liquid vehicle intended for application on different surfaces. The pigment may be inorganic or organic. Examples of inorganic pigments are titanium dioxide, zinc oxide, chromium oxide, iron oxide, carbon black and combinations thereof. Organic pigments can include, for instance, phthalocyanines, azo-compounds, quinacridones, perylenes and others. The vehicle typically contains a binder and a solvent. In case of water based paints the solvent is water. Suitable binders are latex, vinyls, acrylics, alkyds and combinations thereof.

Usually water based paints includes other additives such as dispersants, surfactants, wetting agents, defoamers, driers, extenders, rheology modifiers and coalescent agents.

Varnishes are glossy, transparent coatings mainly used for application on wood, containing a binder and a vehicle. In one embodiment of this invention the use of encapsulated biocides is in water based varnishes, in which the solvent is water. Typical examples of binders used in varnishes are latex, vinyls, acrylics and alkyds.

Usually water based varnishes includes other additives such as dispersants, surfactants, wetting agents, defoamers, driers, rheology modifiers and coalescent agents.

The following examples of compositions were prepared according to examples 1 to 4 described in this patent and illustrate the invention without limiting it thereto. All amounts are given as weight % (w/w).

EXAMPLES

Example 1

Preparation of Smectite Organoclay

Smectite organophilic clays are synthesized from the sodium form of bentonite. First of all 380 g of water is added in a beaker and 20 g of sodium bentonite is slowly added under mechanical stirring and stirred for 20 minutes. Under mechanical stirring 9.13 g of Dodigen® 2808 (benzalkonium chloride) is added and stirred for 60 minutes. The dispersion is left standing at room temperature for 24 hours, after which it is filtered through a buchner funnel. The solid filtered materials are dried at 60° C. for 48 hours and then ground and sieved through a 100 mesh (0.149 mm) sieve.

Example 2

Co-Encapsulation of IPBC Inside of Organoclay

Co-encapsulated IPBC inside of organoclay is synthesized from the sodium form of bentonite. First of all 380 g of water is added in a beaker and 20 g of sodium bentonite is slowly added under mechanical stirring and stirred for 20 minutes. Under mechanical stirring 9.13 g of Dodigen® 2808 (benzalkonium chloride) is added and stirred for 60 minutes. After 5.62 g of Nipacide® IPBC (3-Iodopropynylbutylcarbamate) is added and stirred for more 60 minutes. The dispersion is left standing at room temperature for 24 hours, after which it is filtered through a buchner funnel. The solid filtered materials are dried at 60° C. for 48 hours and then ground and sieved through a 100 mesh (0.149 mm) sieve.

Example 3

Co-Encapsulation of OIT Inside of Organoclay

Co-encapsulation of OIT inside of organoclay is synthesized from the sodium form of bentonite. First of all 380 g of water is added in a beaker and 20 g of sodium bentonite is slowly added under mechanical stirring and stirred for 20 minutes. Under mechanical stirring 9.13 g of Dodigen® 2808 (benzalkonium chloride) is added and stirred for 60 minutes. After 9.47 g of Nipacide® OIT (2-n-octyl-4-isothiazolin-3-one) is added and stirred for more 60 minutes. The dispersion is left standing at room temperature for 24 hours, after which it is filtered through a buchner funnel. The solid filtered materials are dried at 60° C. for 48 hours and then ground and sieved through a 100 mesh (0.149 mm) sieve.

Example 4

Metal Modified Clay Minerals

Metal modified clay mineral is synthesized from the sodium form of bentonite. First of all 380 g of water is added in a beaker and 20 g of sodium bentonite is slowly added under mechanical stirring and stirred for 20 minutes. Under mechanical stirring 4.00 g of Dodigen® 2808 (benzalkonium chloride) is added and stirred for 60 minutes. After 3.11 g of Nipacide® OIT (2-n-octyl-4-isothiazolin-3-one) is added and stirred for more 60 minutes. Finally 1.60 g of Silver nitrate is added and stirred for more 60 minutes. The dispersion is left standing at room temperature for 24 hours, after which it is filtered through a buchner funnel. The solid filtered materials are dried at 60° C. for 48 hours and then ground and sieved through a 100 mesh (0.149 mm) sieve.

Analytical Data

The instant process is using the lipophilic chain of the ammonium quaternary salts as a vehicle to carry on the active ingredients into the layers of the clay minerals. By using this technique it is possible to insert into clay minerals actives without exchanging the sodium of the clay mineral. The process of co-encapsulation of the active ingredients can be shown by X-Ray analysis. After the active ingredient has been encapsulated, a metal with biocidal activity can also be added to the layers of the clay minerals.

Our results using X-Ray analysis show that basal distance between the layers of two tetrahedral sheets condensed with one octahedral sheet in the sodium betonite form is 14.72 Å. After the encapsulation with benzalkonium chloride (Dodigen™ 2808) this basal distance rise up to two diffractions 17.65 Å and 25.21 Å. These two different distances are due the different chain lengths present in the benzalkonium chloride, the first one (17.65 Å) from $C_{12/14}$ chain length and the second one 25.21 Å from $C_{16/18}$ chain.

The X-ray analysis also was used to show the co-encapsulation of IPBC in a clay mineral previously functionalized with benzalkonium chloride (Dodigen® 2808) as described in Example 2. This co-encapsulation of IPBC was observed with basal distances rising from 17.65 Å to 70.60 Å corresponding to the interaction of $C_{12}$-$C_{14}$ chains from benzalkonium chloride and IPBC molecules. Simultaneously, an interaction of $C_{16}$-$C_{18}$ chains from benzalkonium chloride and IPBC molecules occurs. This interaction results in a reduction of basal distance from 25.21 Å to 16.05 Å due to the low concentration of $C_{16-18}$ benzalkonium compounds and because rearrangements occurring between IPBC molecules and the $C_{16-18}$ benzalkonium chain during drying of the product. These alterations of the basal distances show the presence of IPBC co-encapsulated into the clay previously functionalized with benzalkonium chloride (Dodigen® 2808). Another proof of the co-encapsulation of IPBC is available by Scanning Electron Microscopy (SEM) coupled with an Energy Dispersive X-ray Detector (EDS). This method presents a peak around 3.9 keV showing the presence of iodine which came from IPBC. The basal distance of 70.60 Å is equivalent to 7.06 nm showing that IPBC is nanometrically scattered into the clay previously functionalized.

Other analysis methods such as thermogravimetrical analysis (TG) showed in sodium bentonite a mass loss around 10.6% below 100° C. due to mainly water present in the clay. Considering the TG analysis of ammonium quaternary salts encapsulated, the result shows a mass loss of 10.6% of quaternary ammonium salt used in the process. The same results were found when IPBC was co-encapsulated into the clay previously functionalized.

The same behaviour was observed when 2-n-octyl-4-isothiazolin-3-one (OIT) was co-encapsulated. After the co-encapsulation of OIT, silver was anchored into the hydrophobic surface composed of tetra-alkylammonium quaternary salt and OIT. Silver in this case complexes with the nitrogen and sulfur atoms presents in OIT molecules. The complex from silver and OIT is not susceptible to oxidation of silver.

Example 5

Synergism

In order to show the synergism achieved when working the instant invention, benzalkonium chloride and a biocide were encapsulated into a clay mineral. The efficiency of the so obtained composition was determined using the algae contamination avoidance test according to ASTM D5589-97 (2002). The shown concentrations are the minimum concentrations required to prevent algae contamination.

TABLE 1

Minimum Inhibitory Concentration based on active ingredient encapsulated alone and active ingredients co-encapsulated into clay mineral against fungi contamination on dry film (Norm NBR 14941-2003).

| | Active Ingredients [ppm] | |
|---|---|---|
| Products | IPBC | benzalkonium chloride |
| Encapsulated benzalkonium chloride (BKC) | — | >2000 |
| Encapsulated IPBC | 1000 | — |
| IPBC co-encapsulated in organoclay functionalized with benzalkonium chloride | 500 | 600 |

The synergistic effect can be calculated by synergistic index (SI), according to the following formula (F. C. Kull et al., Applied Microbiology, vol. 9 (1961), p. 538):

$$SI = Qa/QA + Qb/QB$$

Wherein:
Qa—concentration (in ppm) of IPBC, in combination with BKC, which produced good results against fungi/algae growth.
QA—concentration (in ppm) of IPBC, as a single biocide, which produced good results against fungi/algae growth.
Qb—concentration (in ppm) of BKC, in combination with IPBC, which produced good results against fungi/algae growth.
QB—concentration (in ppm) of BKC, as single biocide, which produced good results against fungi/algae growth.

A synergistic index<1 corresponds to a synergistic effect. The minimal inhibitory concentration may be regarded as good result. In this example, the SI equals 0.8.

Example 6

A standard water based architectural paint formulation containing the following ingredients was made:

TABLE 2

Composition of the paint formulation

| | % by weight |
|---|---|
| Water | 35.83 |
| Rheological additive (Acrylic associative thickener) | 0.40 |
| Titanium dioxide | 8.00 |
| Calcium carbonate, 325 mesh | 18.00 |
| Talc, 325 mesh | 7.00 |
| Calcium carbonate precipitated | 10.00 |
| Aluminum silicate | 6.00 |
| Ammonia | 0.10 |
| Sodium Nitrite | 0.07 |
| Defoamer (D-Foam-R C113, Clariant) | 0.20 |
| Polyacrylate (Dispersol 589, Clariant) | 0.80 |
| Dioctyl sulfosuccinate (Wetting agent B 70, Clariant) | 0.10 |
| Rheological additive (Acrylic associative thickener) | 1.50 |
| Butylglycol | 0.70 |
| Texanol ®, Eastman | 0.30 |
| Styrene-acrylate copolymer dispersion | 11.00 |

The viscosity of the paint was adjusted with water to 90 KU (Krebs units, measured using the Krebs viscosimeter and spindle at 200 rpm) and the pH with ammonia solution or water to 9.0.

The encapsulated biocide, as described in example 2, was added to the paint during the grinding or let down phase, the encapsulates containing a bentonite, $C_{12}/C_{14}$-alkyldimethyl benzyl ammonium chloride, and 3-iodopropenylbutylcarbamate.

Example 7

Test specimens were prepared by application of two paint coats on watercolor paper (160 g/cm²) for each biocidal composition. After application, test specimens were dried during 7 days. After drying, coated substrates were cut in 30 mm squares.

The test specimens were evaluated after a leaching test where the coated substrates were leached for 8 and 24 hours in 2 L containers of water with a flow rate such that there are 6 changes of the water in a period of 24 hours. Coated substrates were dried to room temperature for 48 hours and then evaluated in terms of microbiological effectiveness.

For the evaluation of antifungal performance on dry film the following test was used:

Sabouraud dextrose agar medium was inoculated with isolated fungi species (*Aspergius niger* ATCC 6275, *Alternaria alternata* ATCC 20084, *Cladosporium cladosporioides* ATCC 16022) in order to have a final concentration of $10^3$ UFC/mL and poured on plates. For each biocidal composition and microorganism, the test was done three times.

The test specimens were placed on the center of the plate and incubated at 27° C. for 14 days. The fungal growth on the sample surface was evaluated using the following scale:
0—No growth visible
1—Up to 10% surface coverage
2—10 to 25% surface coverage
3—25 to 50% surface coverage
4—51 to 75% surface coverage
5—More than 75% surface coverage

TABLE 3

Fungal growth test

| | A. niger ATCC 6275 | A. alternata ATCC 20084 | C. cladosporioides ATCC 16022 |
|---|---|---|---|
| Control (without biocide) | 5 5 5 | 5 5 5 | 5 5 5 |
| 1500 ppm of IPBC 3-iodopropenylbutylcarbamate Nipacide ® IPBC 10 | 4 5 5 | 2 5 5 | 5 5 4 |
| 2000 ppm of IPBC 3-iodopropenylbutylcarbamate Nipacide ® IPBC 10 | 1 1 1 | 0 0 0 | 2 1 1 |
| 500 ppm of IPBC in Encapsulated Biocide of Example 2 | 5 5 5 | 4 4 4 | 3 3 3 |
| 1000 ppm of IPBC in Encapsulated Biocide of Example 2 | 0 0 0 | 0 0 0 | 0 0 0 |

It can be seen from this table that the addition of the encapsulated biocide of Example 2 in an amount that caused 1000 ppm of IPBC to be present was sufficient to prevent fungal growth. This effect cannot even be obtained by the addition of neat IPBC in an amount of 2000 ppm.

The algicidal effect on dry film was evaluated as described bellow:

Inoculums were prepared with a suspension of algae species (*Trentepohlia odorata*, *Chlorella* sp and *Scenedesmus quadricauda*) at concentration of $10^6$ cells/mL. Coated substrates were placed on the center of a pre-poured Bold's Basal Medium agar plates. A thin coat of the algae suspension was applied over the plates. Plates were incubated with humidity ≥85%, 25° C. and cycle of 12 hours light and 12 hours darkness. For each biocidal composition the test was done three times.

The algae growth on the sample surface was evaluated weekly for 3 weeks using the following scale:
0—No growth visible
1—Up to 10% surface coverage
2—10 to 30% surface coverage
3—30 to 60% surface coverage
4—More than 60% surface coverage

TABLE 4

Algae growth test

| | Algae suspension |
|---|---|
| Control (without biocide) | 4 4 4 |
| 1500 ppm of BKC $C_{12}/C_{14}$-alkyldimethyl benzyl ammonium chloride, Dodigen ® 2808 | 4 4 4 |
| 2000 ppm of BKC $C_{12}/C_{14}$-alkyldimethyl benzyl ammonium chloride, Dodigen ® 2808 | 3 3 3 |
| 1000 ppm of BKC in Encapsulated Biocide of Example 2 | 4 3 2 |
| 1500 ppm of BKC in Encapsulated Biocide of Example 2 | 0 0 0 |

It can be seen from this table that the addition of the encapsulated biocide of Example 2 in an amount that caused 1500 ppm of BKC to be present was sufficient to prevent algae growth. This effect cannot nearly be obtained by the addition of neat BKC in an amount of 2000 ppm.

TABLE 5

Conclusion of microbiological test results after leaching:

| | Effective concentration against fungi (ppm relatively to the paint) | Effective concentration against algae (ppm relatively to the paint) |
|---|---|---|
| 3-iodopropenylbutylcarbamate Nipacide ® IPBC 10 | >2000 ppm of IPBC | na |
| $C_{12}/C_{14}$-alkyldimethyl benzyl ammonium chloride, Dodigen ® 2808 | na | >>2000 ppm of BKC |
| Encapsulated Biocide of Example 2 | 1000 ppm of IPBC | 1500 ppm of BKC |

*na = not analysed

Example 8

Additionally, the leaching of biocides was evaluated through a tray test in which 50 g of the a paint formulation containing 1000 ppm of biocidally active agent was applied in the bottom of a tray (23.5×38.0 cm) each time and the painting procedure was repeated twice. The film was dried at room temperature for seven days and then 500 mL of distilled water was added to the tray, after 1, 3, 6 and 24 hours a 10 mL sample were taken and analyzed for determination of the biocides.

TABLE 6

Tray test analysis results

| | $C_{12}/C_{14}$-alkyldimethyl benzyl ammonium chloride, Dodigen ® 2808 | Encapsulated Biocide |
|---|---|---|
| 1 hour | 164 ppm | <50 ppm |
| 3 hours | 177 ppm | <50 ppm |
| 6 hours | 190 ppm | <50 ppm |
| 24 hours | 224 ppm | <50 ppm |

Method's detection limit = 50 ppm

The invention claimed is:

1. A process for the co-encapsulation of biocidally active ingredients in a clay mineral, wherein the process comprises the steps of bringing the clay mineral into contact with a biocidally active nitrogen compound according to formula (4)

$$[R^1R^2(CH_3)_2N]^+X^- \qquad (4)$$

wherein $R^1$ is benzyl, $R^2$ is a linear $C_{12}$ to $C_{18}$ hydrocarbon group and $X^-$ is chloride and at the same time or subsequently bringing the clay mineral into contact with at least one biocidally active compound selected from the group consisting of 2-n-octyl-4-isothiazoline-3-one, 3-iodopropenylbutyl-carbamate, tetrakis(hydroxymethyl)-phosphonium sulfate and mixtures thereof.

2. The process according to claim 1, wherein the clay mineral comprises at least one smectite group mineral in a concentration ranging between 60-95 wt.-%, relative to the total weight of the clay mineral.

3. The process according to claim 1, wherein the biocidally active compound is selected from the group consisting of a binary combination of 2-n-octyl-4-isothiazoline-3-one and 3-iodopropenylbutyl-carbamate, 2-n-octyl-4-isothiazoline-3-one and tetrakis(hydroxymethyl)-phosphonium sulfate, 3-iodopropenylbutyl-carbamate and tetrakis(hydroxymethyl)-phosphonium sulfate, 2-n-octyl-4-isothiazoline-3-one and tetrakis(hydroxymethyl)-phosphonium sulfate and a ternary combination of 2-n-octyl-4-isothiazoline-3-one, 3-iodopropenylbutyl-carbamate and tetrakis(hydroxymethyl)-phosphonium sulfate.

4. The process according to claim 1, further comprising the step of bringing a further biocidally active compound, into contact with the clay mineral, wherein the further biocidally active compound is selected from the group consisting of Ethanol, 1-Propanol, 2-Propanol, 1,2-Propanediol, 2-Phenoxyethanol, 1-Phenoxypropanol, Formaldehyde, Glutaraldehyde, Acetaldehyde, Glyoxal, Ethylene Glycol hemiformal, Ethylene Glycol bishemiformal, 1,3-dioxolane, 3,3'-Methylenebis(5-methyl-1,3-oxazolidine), Hexahydro-1,3,5-tris(2-hydroxyethyl)-s-triazine, Hexahydro-1,3,5-tris(2-hydroxypropyl)-s-triazine, Bis(tetrakis(hydroxymethyl)phosphonium)sulfate, 1,3-Bis(hydroxymethyl)5,5-dimethyl-2,4-dioxoimidazolidine), 6-Acetoxy-2,4-dimethyl-1,3-dioxane, 2,5-Dimethoxytetrahydrofuran, Phenol, Chloromethylphenol, 4-Chlorophenol, Formic acid, Acetic acid, sorbic acid, benzoic acid, boric acid, Ethyl formate, Benzyl bromoacetate, dimethyl dicarbonate, N'-(3,4-dichorophenyl)-N,N-dimethylurea, N'-(4-chlorophenyl)-N'-(3,4-dichlorophenyl)urea), 3-Iodopropynylphenylcarbamate, 3-Iodopropynylcarbamate, Methyl-N-(2-benzimidazolyl)carbamate, 4,4'-Diamidinophenoxypropane, 4,4'-Diamidino-2,2'-dibromodiphenoxypropane, Pyridine-N-oxides, 8-Quinolinol, 1-[2-(2,4-Dichlorophenyl)-4-propyl-1,3-dioxolan-2yl-methyl]1H-1,2,4-triazole, 2-methyl-4-isothiazolin-3-one, 5-Chloro-2-methyl-4-isothiazolin-3-one, 4,5-dichloro-2-(n-octyl)4-isothiazolin-3-one, 1,2-benzisothiazolin-3-one, N-butyl-1,2-benzisothiazolin-3-one), N,N,dimethyl-N'-tolyl-N'-dichlorofluromythylthiosulphamide, 2-Bromoacetamide, 2,2-Dibromo-3-nitrilopropionamide, 2-bromo-2-nitro-propan-1-ol, 2-bromo-2-nitropro-pane-1,3-diol, poly(hexamethylenebiguanide) hydrochloride, sodium ethylmercury thiosalicylate, trichloromelamine and 1,3-dichloro-5,5-dimethylhydantoin.

5. The process according to claim 1, further comprising the step of bringing a metal ion into contact with the clay mineral, wherein the metal ion is selected from the group consisting of silver, copper, zinc, molybdenum and titanium ions.

6. The process according to claim 1, wherein the combined amount of
   a) the biocidally active nitrogen compound according to formula (4) and
   b) OIT, IPBC or THPS or their mixture, and any other biocidally active compounds in the finished biocidally active clay mineral is from 1 to 60 wt.-%, relative to the weight of the finished biocidally active clay mineral.

7. The process according to claim 1, wherein the weight ratio between the biocidally active compound and the biocidally active nitrogen compound according to formula (4) is in the range of 1:10 to 10:1.

8. The process according to claim 5, wherein the total amount of the metal ions, is between 0.5 and 21 wt.-%, the wt.-% being relative to the combined weight of
   a) the biocidally active nitrogen compound according to formula (4)
   b) the metal ions, and,
   c) any other biocidally active compounds.

9. The process according to claim 4, further comprising the step of bringing a metal ion into contact with the clay mineral, wherein the metal ion is selected from the group consisting of silver, copper, zinc, molybdenum and titanium ions.

10. The process according to claim 5, wherein the combined amount of
    a) the biocidally active nitrogen compound according to formula (4),
    b) metal ions, and,
    c) any other biocidally active compound
    in the finished biocidally active clay mineral is from 1 to 60 wt.-%, relative to the weight of the finished biocidally active clay mineral.

11. The process according to claim 9, wherein the total amount of the metal ions, is between 0.5 and 21 wt.-%, the wt.-% being relative to the combined weight of
    a) the biocidally active nitrogen compound according to formula (4),
    b) the metal ions, and,
    c) any other biocidally active compound.

12. The process according to claim 9, wherein the total amount of any other biocidally active compound which is different from a biocidally active nitrogen compound according to formula (4), or 2-n-octyl-4-isothiazoline-3-one (OIT), 3-iodopropenylbutylcarbamate (IPBC) and tetrakis(hydroxymethyl)phosphoniumsulfate (THPS), is between 0.5 and 21 wt.-%, the wt.-% being relative to the combined weight of
    a) the biocidally active nitrogen compound that contains at least one hydrocarbon group with 6 to 20 carbon atoms and
    b) metal ions, and,
    c) any other biocidally active compounds.

* * * * *